(12) United States Patent
Knoer et al.

(10) Patent No.: US 9,657,160 B2
(45) Date of Patent: May 23, 2017

(54) ORGANOPOLYSILOXANE GELS

(71) Applicant: Wacker Chemie AG, Munich (DE)

(72) Inventors: Sebastian Knoer, Emmerting (DE); Aroop Kumar Roy, Mechanicville, NY (US)

(73) Assignee: Wacker Chemie AG, Munich (DE)

( * ) Notice: Subject to any disclaimer, the term of this patent is extended or adjusted under 35 U.S.C. 154(b) by 5 days.

(21) Appl. No.: 14/394,748

(22) PCT Filed: Apr. 11, 2013

(86) PCT No.: PCT/EP2013/057602
§ 371 (c)(1),
(2) Date: Oct. 16, 2014

(87) PCT Pub. No.: WO2013/156390
PCT Pub. Date: Oct. 24, 2013

(65) Prior Publication Data
US 2015/0073059 A1    Mar. 12, 2015

(30) Foreign Application Priority Data

Apr. 16, 2012 (DE) .................. 10 2012 206 209

(51) Int. Cl.
| | | |
|---|---|---|
| *A61K 8/04* | (2006.01) |
| *A61K 8/89* | (2006.01) |
| *A61Q 19/00* | (2006.01) |
| *A61Q 1/02* | (2006.01) |
| *C08K 5/01* | (2006.01) |
| *C08K 5/548* | (2006.01) |
| *A61K 8/895* | (2006.01) |
| *C08L 83/04* | (2006.01) |
| *C08K 5/101* | (2006.01) |
| *C08K 5/54* | (2006.01) |
| *C08G 77/12* | (2006.01) |
| *C08G 77/20* | (2006.01) |

(52) U.S. Cl.
CPC .............. *C08K 5/548* (2013.01); *A61K 8/042* (2013.01); *A61K 8/89* (2013.01); *A61K 8/895* (2013.01); *A61Q 1/02* (2013.01); *A61Q 19/00* (2013.01); *A61Q 19/008* (2013.01); *C08K 5/01* (2013.01); *C08K 5/101* (2013.01); *C08K 5/5403* (2013.01); *C08L 83/04* (2013.01); *C08G 77/12* (2013.01); *C08G 77/20* (2013.01)

(58) Field of Classification Search
CPC .......... C08L 83/04; C08L 83/00; C08K 5/56; A61K 8/042; A61K 8/89
See application file for complete search history.

(56) References Cited

U.S. PATENT DOCUMENTS

| | | |
|---|---|---|
| 6,200,581 B1 | 3/2001 | Lin et al. |
| 6,365,670 B1 | 4/2002 | Fry |
| 6,423,322 B1 | 7/2002 | Fry |
| 2003/0095935 A1 | 5/2003 | Chaiyawat et al. |
| 2004/0105828 A1 | 6/2004 | Chaiyawat et al. |

FOREIGN PATENT DOCUMENTS

WO    2011/059106 A1    5/2011

OTHER PUBLICATIONS

International Search Report for PCT/EP2013/057602, completed by the European Patent Office on May 14, 2013, 2 pages.

*Primary Examiner* — Alma Pipic
(74) *Attorney, Agent, or Firm* — Brooks Kushman P.C.

(57) ABSTRACT

Organopolysiloxane gels produced by crosslinking an unsaturated organopolysiloxane resin with a crosslinking agent in the presence of a diluent have excellent sensory properties such as properties desirable in a variety of cosmetics products.

19 Claims, No Drawings

ORGANOPOLYSILOXANE GELS

CROSS-REFERENCE TO RELATED APPLICATIONS

This application is the U.S. National Phase of PCT Appln. No. PCT/EP2013/057602 filed Apr. 11, 2013, which claims priority to German application DE 10 2012 206 209.2 filed Apr. 16, 2012, the disclosures of which are incorporated in their entirety by reference herein.

BACKGROUND OF THE INVENTION

1. Field of the Invention

The invention relates to organopolysiloxane gels, methods of production thereof, and application thereof in cosmetic formulations.

2. Description of the Related Art

The organopolysiloxane gels of the present invention are produced by crosslinking an unsaturated organopolysiloxane resin with a special Si—H-containing organopolysiloxane, also called Si—H-functional crosslinking agent, in the presence of a diluent.

Crosslinked materials are polymer chains linked together in a three-dimensional network. They can be regarded as long-chain branchings, which are so numerous that a continuous, insoluble network or gel is formed.

Organopolysiloxane networks are often produced in platinum-catalyzed hydrosilylation reactions. Often a Si—H-containing organopolysiloxane and a vinyl-functional organopolysiloxane are reacted together. An essential precondition for the formation of a three-dimensional network is that at least one of the two components, the Si—H-containing organopolysiloxane or the vinyl-functional organopolysiloxane, has more than two functionalities per molecule in its average composition.

The platinum-catalyzed hydrosilylation reaction has the advantage that no by-products are formed in the formation of organopolysiloxane networks, and that linkage points and network architecture are narrowly defined. The most important reason for using organopolysiloxane gels in cosmetic applications is the resultant sensory advantages, especially the improved feel of cosmetic formulations on the skin. Furthermore, organopolysiloxane gels are used as thickening agents in cosmetic formulations.

U.S. Pat. No. 6,423,322 B1 discloses organopolysiloxane gels, which can be easily produced by a hydrosilylation reaction of a special, vinyl-functional MQ resin with a highly Si—H-containing organopolysiloxane with about 0.5 wt. % of silicon-bonded hydrogen atoms in the presence of decamethylcyclopentasiloxane as diluent, and a small amount of platinum hydrosilylation catalyst. The resultant gels are nonstringy and can be easily homogenized to a stable cream or paste. However, a substantial drawback of these organopolysiloxane gels is the resultant feel on the skin, which is not ideal for cosmetic applications.

Furthermore, as is the case with many organic diluents that are often used in cosmetic applications, suitable gels cannot be produced if an Si—H-containing organopolysiloxane with comparatively high content of silicon-bonded hydrogen atoms is used as Si—H-functional crosslinking agent. Therefore, the sometimes low compatibility of the gels with organic compounds and diluents is a disadvantage in the production of cosmetic formulations. Owing to the relatively high proportion of vinyl-functional MQ resin, such gels are also comparatively expensive to produce.

US 2004/0105828 A1 and US 2003/0095935 A1 describe a number of different silicone gels, including gels that are obtained by a hydrosilylation reaction of a Si—H-containing polysiloxane and an unsaturated MQ resin in a diluent. Improved transfer resistance is cited as an important advantage. However, there are no examples in which the production and the action of these organopolysiloxane gels are demonstrated.

The problem was to provide new organopolysiloxane gels with improved properties, in particular with an improved feel on the skin, which do not have the aforementioned disadvantages.

SUMMARY OF THE INVENTION

It has not been unexpectedly and surprisingly discovered that gels produced with a Si—H-containing organopolysiloxanes or an Si—H-containing organopolysiloxane mixture have improved compatibility with organic diluents. Such gels have far better sensory properties, in particular a better feel on the skin, than gels based on an organopolysiloxane with relatively high content of silicon-bonded hydrogen atoms. Furthermore, these gels are stable in storage and are very suitable for a variety of cosmetic applications.

DESCRIPTION OF THE PREFERRED EMBODIMENTS

The invention relates to organopolysiloxane gels produced by reaction of (1) unsaturated organopolysiloxane resins with
(2) Si—H functional organopolysiloxanes of the general formula $$H_c R_{3-c} SiO(R_2SiO)_a(RHSiO)_b SiR_{3-c}H_c \quad (I),$$

wherein
c is 0 or 1, preferably 0,
R can be identical or different and is a monovalent, optionally substituted hydrocarbon residue with 1 to 18 carbon atoms per residue,
a and b are integers, with the proviso that
the sum a+b is 66 to 248, preferably 98 to 248, more preferably 118 to 168,
that the organopolysiloxanes (2) contain Si-bonded hydrogen in amounts from 0.011 to 0.044 wt. %, preferably from 0.019 to 0.044 wt. %, more preferably from 0.022 to 0.032 wt. %,
and that the number of Si—H groups per molecule in the average composition is greater than 2,
or mixtures of (2) Si—H functional organopolysiloxanes with (2') Si—H functional organopolysiloxanes of the general formula $$H_c R_{3-c} SiO(R_2SiO)_a(RHSiO)_b SiR_{3-c}H_c \quad (I'),$$

wherein
c is 0 or 1, preferably 0,
R has the same meaning as above, a and b are integers, with the proviso that
the sum a+b is 8 to 248, preferably 38 to 248,
and that the organopolysiloxanes (2') contain Si-bonded hydrogen in amounts from 0.045 to 0.35 wt. %, preferably from 0.045 to 0.156 wt. %,
carried out with the proviso that if mixtures of (2) and (2') are used, the weight ratio of (2) to (2') is preferably greater than 0.2, most preferably greater than 0.3,
in the presence of
(3) catalysts promoting the addition of Si-bonded hydrogen to aliphatic multiple bond, wherein (1) and (2) or mixtures of (2) and (2') are dispersed in
(4) diluents, preferably organopolysiloxanes with 2 to 200 Si atoms, preferably organopolysiloxanes with 2 to 50 Si atoms, or organic diluents.

The invention further relates to a method of production of the organopolysiloxane gels by reacting
(1) unsaturated organopolysiloxane resins with
(2) Si—H functional organopolysiloxanes of the general formula $$H_cR_{3-c}SiO(R_2SiO)_a(RHSiO)_bSiR_{3-c}H_c \qquad (I),$$

wherein
c is 0 or 1, preferably 0,
R can be identical or different and is a monovalent, optionally substituted hydrocarbon residue with 1 to 18 carbon atoms per residue,
a and b are integers, with the proviso that
the sum a+b is 66 to 248, preferably 98 to 248, more preferably 118 to 168,
that the organopolysiloxanes (2) contain Si-bonded hydrogen in amounts from 0.011 to 0.044 wt. %, preferably from 0.019 to 0.044 wt. %, more preferably from 0.022 to 0.032 wt. %,
and that the number of Si—H groups per molecule in the average composition is greater than 2,
or mixtures of (2) Si—H functional organopolysiloxanes with (2') Si—H functional organopolysiloxanes of the general formula $$H_cR_{3-c}SiO(R_2SiO)_a(RHSiO)_bSiR_{3-c}H_c \qquad (I'),$$

wherein
c is 0 or 1, preferably 0,
R has the same meaning as above, a and b are integers, with the proviso that
the sum a+b is 8 to 248, preferably 38 to 248,
and that the organopolysiloxanes (2') contain Si-bonded hydrogen in amounts from 0.045 to 0.35 wt. %, preferably from 0.045 to 0.156 wt. %,
carried out
with the proviso that if mixtures of (2) and (2') are used, the weight ratio of (2) to (2') is preferably greater than 0.2, especially preferably greater than 0.3,
in the presence of
(3) catalysts promoting the addition of Si-bonded hydrogen to aliphatic multiple bond,
wherein (1) and (2) or mixtures of (2) and (2') are dispersed in
(4) diluents, preferably organopolysiloxanes with 2 to 200 Si atoms, preferably organopolysiloxanes with 2 to 50 Si atoms, or organic diluents.

In the context of this invention, formulas (I) and (I') are to be understood such that a units —(R$_2$SiO)— and b units —(RHSiO)— can be distributed arbitrarily in the organopolysiloxane molecule.

The Si—H-containing organopolysiloxanes (2) used preferably have a viscosity from 50 to 2000 mm$^2$/s, more preferably 100 to 1000 mm$^2$/s, most preferably 150 to 600 mm$^2$/s, in each case at 25° C., and a molar ratio a:(b+c) of preferably 30:1 to 150:1, more preferably 30:1 to 80:1, most preferably 40:1 to 70:1. The Si—H-containing organopolysiloxanes (2') used in the mixtures with (2) preferably have a viscosity from 3 to 2000 mm$^2$/s, most preferably 20 to 1200 mm$^2$/s, in each case at 25° C., and a molar ratio a:(b+c) of preferably 4:1 to 30:1, most preferably 8:1 to 30:1.

It was found, surprisingly, that the organopolysiloxane gels based on the Si—H-containing organopolysiloxanes (2) or based on the mixture of (2) and (2') have far better sensory properties, in particular a better feel on the skin, than gels based on an organopolysiloxane with relatively high content of silicon-bonded hydrogen atoms such as are disclosed in U.S. Pat. No. 6,423,322 B1. They are extremely slippery and do not have an undesirable oily feel. After being distributed on the skin, they leave the skin feeling more supple, without any undesirable film-like or dull feel.

Examples of residues R are alkyl residues such as the methyl, ethyl, n-propyl, iso-propyl, 1-n-butyl, 2-n-butyl, iso-butyl, tert-butyl, n-pentyl, iso-pentyl, neo-pentyl, tert-pentyl residue, hexyl residues such as the n-hexyl residue, heptyl residues such as the n-heptyl residue, octyl residues such as the n-octyl residue, iso-octyl residues such as the 2,2,4-trimethylpentyl residue, nonyl residues such as the n-nonyl residue, decyl residues such as the n-decyl residue, dodecyl residues such as the n-dodecyl residue, and octadecyl residues such as the n-octadecyl residue; cycloalkyl residues such as cyclopentyl, cyclohexyl, cycloheptyl, and methylcyclohexyl residues; aryl residues such as the phenyl, naphthyl, anthryl, and phenanthryl residue; alkaryl residues such as o-, m-, p-tolyl residues, xylyl residues, and ethylphenyl residues; and aralkyl residues such as the benzyl residue, the α- and the β-phenylethyl residue.

Examples of substituted residues R are haloalkyl residues such as the 3,3,3-trifluoro-n-propyl residue, the 2,2,2',2', 2'-hexafluoroisopropyl residue, the heptafluoroisopropyl residue, and haloaryl residues such as the o-, m-, and p-chlorophenyl residue.

Preferably, the residue R is a monovalent hydrocarbon residue with 1 to 6 carbon atoms, the methyl residue being especially preferred.

The unsaturated organopolysiloxane resins (1) used in the organopolysiloxane gels are preferably unsaturated organopolysiloxane resins made up of units of the general formula (II)

$$R_xR'_ySiO_{(4-x-y)/2} \qquad (II),$$

wherein
R has the same meaning as above,
R' represents a monovalent hydrocarbon residue, onto which Si—H groups can be added in a hydrosilylation reaction, preferably represents a monovalent hydrocarbon residue with 2 to 18 carbon atoms having a terminal, aliphatic C—C multiple bond,
preferably an ω-alkenyl residue with 2 to 12 carbon atoms, most preferably a vinyl residue,
x is 0, 1, 2, or 3,
y is 0, 1, or 2, preferably 0 or 1,
with the proviso that the sum x+y is less than or equal to 3, and that per molecule at least 2 residues R', preferably at least 3 residues R', at least 20 mol. % T and/or Q units (T units: sum x+y=1; Q units: sum x+y=0), preferably at least 20 mol. % Q units, must be present, and in addition D units (sum x+y=2) can be present.

Preferably the unsaturated organopolysiloxane resins of formula (II) are
MQ resins from units of the formulas
SiO$_2$ (Q units) and
R$_3$SiO$_{1/2}$ and R$_2$R'SiO$_{1/2}$ (M units),
wherein R and R' have the same meaning given as above.

The molar ratio of M to Q units is in this case preferably in the range from 0.5 to 4.0, more preferably in the range from 0.5 to 2.0, most preferably in the range from 0.6 to 1.5. These silicone resins can moreover contain up to 10 wt. % of free hydroxyl or alkoxy groups.

The unsaturated organopolysiloxane resins (1) preferably have a viscosity greater than 0.7 mm$^2$/s at 25° C., and more preferably a viscosity greater than 1000 mm$^2$/s at 25° C., or the organopolysiloxane resins are solids. The weight-average molecular weight $M_w$, determined by gel permeation chromatography (relative to a polystyrene standard) of these resins is preferably 334 to 200,000 g/mol, more preferably 1000 to 20,000 g/mol.

The unsaturated organopolysiloxane resins (1) of the organopolysiloxane gels preferably have an iodine number below 254, and organopolysiloxane resins with an iodine number below 76 are preferred. The unsaturated hydrocarbon residue is preferably bound to an M unit (=$M_{Vi}$) or D unit (=$D_{Vi}$) preferably to an M unit, wherein the molar ratio M:($M_{Vi}$+$D_{Vi}$), preferably M:$M_{Vi}$, is preferably in the range from 0 to 50, more preferably in the range from 0 to 20, most preferably in the range from 2.5 to 13.

Examples of residues R' are alkenyl residues, such as the vinyl, 5-hexenyl, cyclohexenyl, 1-propenyl, allyl, 3-butenyl and 4-pentenyl residue, and alkynyl residues, such as the ethynyl, propargyl and 1-propynyl residue. Preferably the residue R' denotes alkenyl residues, more preferably ω-alkenyl residues, in particular the vinyl residue.

For the organopolysiloxane gels, unsaturated organopolysiloxane resins (1) are used in amounts of preferably 4.5 to 0.1 mol, more preferably 2 to 0.8 mol, most preferably 1.8 to 1.1 mol, hydrocarbon residue with aliphatic C—C multiple bond per mol of Si-bonded hydrogen in Si—H functional organopolysiloxanes (2) and (2').

The weight ratio of MQ resin to the Si—H-containing organopolysiloxane in the organopolysiloxane gels disclosed in U.S. Pat. No. 6,423,322 B1 is in the range from 7 to 4. The high proportion of comparatively expensive resin makes these gels comparatively expensive. In the organopolysiloxane gels, the weight ratio of the unsaturated organopolysiloxane resins (1) to the Si—H-containing organopolysiloxanes (2) is preferably in the range from 3 to 0.1, more preferably in the range from 2.0 to 0.1, and most preferably in the range from 1 to 0.1. In the organopolysiloxane gels, the weight ratio of the unsaturated organopolysiloxane resins (1) to the mixtures of the Si—H-containing organopolysiloxanes (2) and (2') is preferably in the range from 3 to 0.1, more preferably in the range from 2.5 to 0.1, and most preferably in the range from 2.2 to 0.1.

The same catalysts can be used as catalyst (3) as have been used until now for promoting the addition of Si-bonded hydrogen onto aliphatic multiple bonds. The catalysts are preferably a metal from the platinum metal group or a compound, or a complex from the platinum metal group. Examples of the catalysts are metallic and finely-divided platinum, which can be on supports such as silicon dioxide, aluminum oxide or activated charcoal, compounds or complexes of platinum such as platinum halides, e.g. PtCl$_4$, H$_2$PtCl$_6$.6H$_2$O, Na$_2$PtCl$_4$.4H$_2$O, platinum-olefin complexes, platinum-alcohol complexes, platinum-alcoholate complexes, platinum-ether complexes, platinum-aldehyde complexes, platinum-ketone complexes, including reaction products from H$_2$PtCl$_6$.6H$_2$O and cyclohexanone, platinum-vinyl-siloxane complexes such as platinum-1,3-divinyl-1,1,3,3-tetramethyl-disiloxane complexes containing or not containing detectable inorganically bound halogen, bis(γ-picoline)-platinum dichloride, trimethylenedipyridine platinum dichloride, dicyclopentadiene platinum dichloride, dimethylsulfoxydethylene-platinum-(II)-dichloride, cyclooctadiene-platinum dichloride, norbornadiene-platinum dichloride, γ-picoline-platinum dichloride, cyclopentadiene-platinum dichloride, and reaction products of platinum tetrachloride with olefin and primary amine or secondary amine or primary and secondary amine such as the reaction product from platinum tetrachloride dissolved in 1-octene with sec-butylamine or ammonium-platinum complexes. Preferred hydrosilylation catalysts are platinum compounds that are in a solvent suitable for use in cosmetic formulations.

The catalyst (3) is preferably used in amounts from 1 to 50 wt-ppm (parts by weight per million parts by weight), most preferably 2 to 20 wt-ppm, in each case calculated as elemental platinum and relative to the total weight of the unsaturated organopolysiloxane resins (1), of the Si—H functional organopolysiloxanes (2) or of the mixture of the Si—H functional organopolysiloxanes (2) and (2') and the diluent (4).

The organopolysiloxane gels preferably contain 1 to 98 wt. % of diluent, more preferably 50 to 95 wt. % of diluent, relative to the total weight of the organopolysiloxane gels.

Unreactive or relatively unreactive diluents are preferred. In the context of the present invention, the term "unreactive" is used with reference to the crosslinking reaction in question and the reactants used herein. A relatively unreactive diluent is less than a tenth as reactive with the reactants of the crosslinking reaction than the reactants reacting with one another in the crosslinking reaction.

Suitable examples of diluents comprise cyclic and linear organopolysiloxanes, organic diluents or mixtures of organopolysiloxanes, and organic diluents.

The organopolysiloxane can be an individual organopolysiloxane or a mixture of organopolysiloxanes. The organopolysiloxane can bear alkyl, aryl, alkaryl, and aralkyl groups. The organopolysiloxanes can, for example, be represented by polydimethylsiloxane, polydiethylsilane, polymethylethylsiloxane, polymethylphenylsiloxane, and polydiphenylsiloxane, but are not restricted to these.

It is also possible to use functional organopolysiloxanes, for example acrylamide functional siloxane fluids, acrylic functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, and silano functional siloxanes.

Cyclic polydimethylsiloxanes can, for example, be represented by hexamethylcyclotrisiloxane, octamethylcyclotetrasiloxane, decamethylcyclopentasiloxane and dodecamethylcyclohexasiloxane, but are not restricted to these.

Preferably, the organopolysiloxane is a polydimethylsiloxane with 2 to 200 Si atoms, more preferably 2 to 50 Si atoms, and most preferably linear polydimethylsiloxanes with a viscosity from 1.5 to 50 mm$^2$/s at 25° C.

Aromatic hydrocarbons, alcohols, aldehydes, ketones, amines, esters, ethers, alkyl halides, or aromatic halides can be used as organic diluents. Representative examples are alcohols such as methanol, ethanol, i-propanol, cyclohexanol, benzyl alcohol, 2-octanol, ethylene glycol, propylene glycol, and glycerol; aliphatic hydrocarbons such as pentane, cyclohexane, heptane, white spirits; alkyl halides such as chloroform, carbon tetrachloride, perchloroethylene, ethyl chloride, and chlorobenzene; aromatic hydrocarbons such as benzene, toluene, ethylbenzene, and xylene; esters of carboxylic acids with 2 to 30 carbon atoms such as ethyl acetate, isopropyl acetate, ethyl acetoacetate, amyl acetate, isobutyl isobutyrate, benzyl acetate, isopropyl palmitate, and isopropyl myristate (=myristic acid isopropyl ester); ethers such as ethyl ether, n-butyl ether, tetrahydrofuran, and 1,4-dioxane; ketones such as acetone, methyl ethyl ketone, cyclohexanone, diacetone alcohol, methyl amyl ketone, and diisobutyl ketone; fatty oils including polyunsaturated ω-3 and ω-6 fatty acids and esters thereof; vegetable oils such as peanut oil, olive oil, palm oil, canola oil, corn oil, soybean oil, sunflower oil, and the like; and natural and synthetic oils or oil-soluble solids such as various mono-, di-, and triglycerides, polyalkoxylated vegetable oils, lanolin, lecithin, and the like; and petroleum hydrocarbons such as petroleum jelly, mineral oil, gasoline, petroleum ether. These examples are provided for explanation and are not to be understood as any limitation.

Other mixed organic diluents can also be used such as acetonitrile, nitromethane, dimethylformamide, propylene oxide, trioctyl phosphate, butyrolactone, furfural, pine oil, turpentine, and m-cresol.

Suitable organic diluents are also volatile aromatic substances such as peppermint oil, green mint oil, menthol, vanilla, cinnamon oil, clove oil, bay oil, anise oil, *eucalyptus* oil, thyme oil, cedar oil, nutmeg oil, sage oil, *cassia* oil, cocoa, licorice, corn syrup with high fructose content, citrus oils such as lemon, orange, lime and grapefruit, fruit essences such as apple, pear, peach, grape, strawberry, raspberry, cherry, plum, pineapple, and apricot; and other useful aromatic substances including aldehydes and esters such as cinnamic acid ethyl acetate, cinnamaldehyde, eugenyl formate, p-methylanisole, acetaldehyde, benzaldehyde, anisaldehyde, citral, neral, decanal, vanillin, tolyl aldehyde, 2,6-dimethyloctanal, and 2-ethylbutyraldehyde.

A portion or the whole organic diluent can comprise one or more volatile odorants such as natural products and perfume oils. Some representative natural products and perfume oils are amber, benzoin, civet, clove, cedar oil, jasmine, maté, *mimosa*, musk, myrrh, iris, sandalwood oil, and vetiver oil; aroma chemicals such as amyl salicylate, amyl cinnamaldehyde, benzyl acetate, citronellol, coumarin, geraniol, isobornyl acetate, ambrette and terpinyl acetate, and various classical perfume oil families such as the floral bouquet family, the oriental family, the Chypre family, the wood family, the citrus family, the Canoe family, the leather family, the spice family, and the herb family.

The organic diluent can also comprise aliphatic or alicyclic hydrocarbons with 4 to 30 carbon atoms, preferably saturated hydrocarbons. The aliphatic hydrocarbons can be linear or branched, and the alicyclic hydrocarbons can represent unsubstituted cyclic hydrocarbons or aliphatic hydrocarbon-substituted hydrocarbons. Examples of suitable hydrocarbons are n-heptane, n-octane, isooctane, n-decane, isodecane, n-dodecane, isododecane, cyclohexane, cycloheptane, cyclooctane, methylcyclohexane, dimethylcyclohexane, ethylcyclohexane, nonylcyclohexane, and the like. This list is also provided for explanation and is not to be understood limiting.

Other suitable organic diluents are oil-like polyethers such as bis(alkyl)ethers of low-molecular glycols and liquid oligomeric and polymeric polyoxyalkylene glycols, and alkyl mono- and diethers, and mono- and dialkyl esters thereof. Preferably, the major part of the polyoxyalkylene glycols is produced from a major part (>50 mol. %) of alkylene oxides with more than two carbon atoms, i.e. propylene oxide, 1,2- and 2,3-butylene oxide, tetrahydrofuran, oxetane, cyclohexene oxide, and the like.

Preferred organic diluents have a viscosity in the range from 0.5 to 200 mm$^2$/s (25° C.), the diluents with a boiling point in the range from 50° C. to 300° C. being especially preferred.

Numerous mixtures of diluents can be used, which are only limited to those compositions with which no phase separation occurs after producing the organopolysiloxane gel.

It was found, as a complete surprise, that the gels produced with an Si—H-containing organopolysiloxane (2) or an Si—H-containing organopolysiloxane mixture of (2) and (2'), have improved compatibility with organic diluents. Creamy gels that are stable in storage and are eminently suitable for cosmetic applications are obtained. In contrast, suitable gels that are stable in storage could not be produced in organic diluents when Si—H-containing organopolysiloxanes with comparatively high content of silicon-bonded hydrogen, as disclosed in U.S. Pat. No. 6,423,322 B1, were used.

Production of the gel can be carried out easily. In general, all ingredients except the catalyst are added, stirred slowly, until a homogeneous mixture is obtained, and then the catalyst is added, stirring continuously. The composition can be left at room temperature until a gel forms, or it can be heated. Preferably, the composition is heated to a temperature between 50° C. and 130° C. and more preferably between 70° C. and 120° C., until the mixture gels or becomes solid. Gelation takes place preferably within ten hours, more preferably within three hours. Organopolysiloxane gels that are obtained are suitable for use in cosmetic formulations.

In an optional second step, the organopolysiloxane gel obtained in the first step is homogenized to a creamy consistency using standard high-shear mixing techniques. This can be effected by intensive mixing and dispersing in rotor-stator stirrers, colloid mills, high-pressure homogenizers, microchannels, membranes, jet nozzles, and the like, or by means of ultrasound. Homogenizing equipment and processes are described for example in Ullmann's Encyclopedia of Industrial Chemistry, CD-ROM Edition 2003, Wiley-VCH Verlag, under the headword "Emulsions".

In an optional third step, a further amount of diluent is added to the organopolysiloxane gel obtained after the first or optional second steps. In this way it is possible, starting from a "basis gel" obtained in the first step, to produce a large number of different gels, which vary widely in their consistency and their property profile. It is possible to use the same diluent as was used in the first step or a second diluent comprising those described previously as diluent herein. Alternatively, any mixture of the diluents already described herein and/or an active substance for body care or health care, or a mixture of an active substance for body care or health care with one or more of the diluents described herein can also be added, with the proviso that no phase separation occurs.

As used herein, a "personal care or healthcare active ingredient" means any compound or mixtures of compounds that are known in the art as additives in the personal care formulations that are typically added for the purpose of treating hair or skin to provide a cosmetic and/or aesthetic benefit, any compound or mixtures of compounds that are known in the art to provide a pharmaceutical or medical benefit; any compound that is intended to furnish pharmacological activity or other direct effect in the diagnosis, cure, mitigation, treatment, or prevention of disease, or to affect the structure or any function of the body of a human or animals; and any compound that may undergo chemical change in the manufacture of drug products and be present in drug products in a modified form intended to furnish the specified activity or effect. Thus, "personal care and healthcare active ingredient" includes, but is not limited to, an active ingredient or an active drug ingredient as generally used and defined by the United States Department of Health & Human Services Food and Drug Administration, contained in Title 21, Chapter I, of the Code of Federal Regulations, Parts 200-299 and Parts 300-499.

The active substances for body care or health care are preferably selected from the group of fat-soluble or oil-soluble vitamins, oil-soluble medicinal products, wherein antiacne agents, antibacterial agents, fungicidal agents, anti-inflammatory agents, antipsoriatic agents, anesthetics, antipruritic agents, antidermatitis agents and agents that are generally regarded as barrier films are especially preferred, and oil-soluble UV absorbers.

Useful active ingredients for use in step 3 of the method comprise fat-soluble and oil-soluble vitamins. Useful oil-soluble vitamins comprise, but are not limited to, vitamin $A_1$, RETINOL, $C_2$ to $C_{18}$ esters of RETINOL, vitamin E, TOCOPHEROL, esters of vitamin E and mixtures thereof. RETINOL comprises trans-RETINOL, 13-cis-RETINOL, 11-cis-RETINOL, 9-cis-RETINOL, and 3,4-didehydro-RETINOL. The oil-soluble vitamin can be used in the composition in amounts from 0.01 to 50 wt. %.

It should be pointed out that RETINOL is an International Nomenclature Cosmetic Ingredient (INCI) name, assigned by The Cosmetic, Toiletry, and Fragrance Association (CTFA), Washington D.C., for vitamin A. Other suitable vitamins and the INCI names for the vitamins in question that are comprised herein are RETINYL ACETATE, RETINYL PALMITATE, RETINYL PROPIONATE, a-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE.

Some examples of commercially available products that are suitable for use herein are Vitamin-A-Acetate, Fluka Chemie AG, Buchs, Switzerland; CIOVI-OX T-50, a vitamin E product from Henkel Corporation, La Grange, Ill.; COVI-OX T-70, another vitamin E product from Henkel Corporation, La Grange, Ill., and Vitamin-E-Acetate, a product from Roche Vitamins & Fine Chemicals, Nutley, N.J.

Representative examples of some suitable oil-soluble medicinal products that can be added as active ingredients in the third step according to the invention are clonidine, scopolamine, propranolol, estradiol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

The following are also comprised herein as a medicinal product for the purposes of the present invention: antiacne agents such as benzoyl peroxide, triclosan, and tretinoin; antibacterial agents such as chlorhexidine gluconate; fungicidal agents such as miconazole nitrate; anti-inflammatory agents such as salicylic acid; corticosteroid drugs; nonsteroidal anti-inflammatory agents such as diclofenac; antipsoriatic agents such as clobetasol propionate and retinoids; anesthetics such as lidocaine; antipruritic agents such as polidocanol; antidermatitis agents such as prednisolone; and agents that are generally regarded as barrier films.

Representative examples of oil-soluble UV absorbers that can be added as active ingredients in the third step are 1-(4-methoxyphenyl)-3-(4-tert-butylphenyl)propane-1,3-dione (INCI: butyl methoxydibenzoylmethane), 2-ethylhexyl-(2E)-3-(4-methoxyphenyl)prop-2-enoate (INCI: octyl methoxycinnamate), 4-hydroxy-2-methoxy-5-(oxo-phenyl-methyl)benzenesulfonic acid (INCI: benzophenone-4), 2-hydroxy-4-methoxybenzophenone-5-sulfonic acid sodium salt (INCI: benzophenone-5) and 2-ethylhexyl-2-hydroxybenzoate (INCI: ethylhexylsalicylate).

Preferably, in a fourth step, the organopolysiloxane gel obtained after the first or optional second, or optional third step is homogenized to a creamy consistency using standard high-shear mixing techniques. Suitable technologies for this are noted above. If an additional amount of diluent was added in the optional third step, this will be distributed homogeneously in the gel in the fourth step. The gel swells and its softness changes.

"Creamy." referring to the gel, means that the starting gel has been sheared to a creamy consistency. The resultant creamy gel can be pourable or relatively stiff, depending on circumstances. The attribute "creamy" distinguishes these sheared gels, which may be transparent or opaque, from the gels produced immediately as a result of gelation of the reactive ingredients.

"Stable in storage" means, in the context of this invention, that the organopolysiloxane gels formed do not separate into two or more phases within 6 months of storage at room temperature, and the softness of the gel does not change substantially during this period.

Preferably, a hydrosilylation catalyst poison or an SiH-quencher is added to the organopolysiloxane gel to stop the postcuring that is caused by residual crosslinking hydrosilylation reactions that take place in the silicone elastomers. Examples of hydrosilylation catalyst poisons or SiH-quenchers that are suitable for stopping postcuring are organosulfur compounds. Other suitable compounds are mentioned in U.S. Pat. No. 6,200,581. Preferred hydrosilylation catalyst poisons are mercaptoalkyl organopolysiloxanes with mercaptopropyl-functional silsesquisiloxanes or mercaptopropyl-functional polyorganosiloxanes being especially preferred, which are preferably used in amounts from 200 to 1.0 mol, more preferably from 50 to 1.5 mol, most preferably from 20 to 2.0 mol, of mercapto groups per mol of platinum atoms. Addition of the hydrosilylation catalyst poison or the SiH-quencher can take place in any one or more of the aforementioned steps.

The organopolysiloxane gels are most preferably suitable for cosmetic applications, and are therefore preferably used in cosmetic compositions. They are, however, also suitable for other applications, for example for medical and technical applications.

The organopolysiloxane gels are particularly valuable in body care products. They can be spread gently on the skin and can therefore be used alone or can be mixed with other body care product ingredients to form a large number of body care products.

Examples of ingredients of body care products are esters, waxes, oils and fats of animal or plant origin, fatty alcohols, fatty acids, alkyl esters of fatty acids, hydrocarbons and hydrocarbon waxes, water, organic solvents, perfumes, surfactants, oil-soluble vitamins, water-soluble vitamins, oil-soluble medicinal products, water-soluble medicinal products, UV absorbers, active pharmaceutical compounds, and others.

In particular, the organopolysiloxane gels are suitable in antiperspirants and deodorizing antiperspirants as they leave a dry feel and do not cool the skin during evaporation. They are slippery and improve the properties of skin creams, skin care lotions, moisturizers, facial treatments such as acne or wrinkle removers, body and face cleansers, bath oils, perfumes, eau de cologne, sachets, sunscreens, preshave and aftershave lotions, liquid soaps, shaving soaps, and shaving foams. They can be used in hair shampoos, hair conditioners, hair sprays, mousses, hair perming agents, depilatories and cuticle coverings, to improve gloss and dry slip, and provide conditioning advantages.

In cosmetics, they function as distributing agents for pigments in make-up, coloring cosmetics, foundations, rouge, lipsticks, lip balsam, eye liner, mascara, oil removers, and coloring cosmetic removers. They are suitable as delivery systems for oil-soluble active ingredients stated as examples herein, e.g. vitamins, medicinal products, and UV absorbers. When they are used in sticks, gels, lotions, and roll-ons, the elastomers impart a dry, silky soft feel. When incorporated in cosmetics and other skin care products, the elastomers impart a matting effect.

In addition, the organopolysiloxane gels display a large number of advantageous properties, e.g. clarity, storage stability, and simplicity of manufacture. Therefore, they have a wide field of application, in particular in antiperspirants, deodorants, skin care products, in perfumes as carriers, and for hair conditioning.

The organopolysiloxane gels have uses beyond the field of body care, including applications as fillers or insulating materials for electric cables, soil, or water barriers for soil stabilization, or as an substitute for epoxy materials that are used in components in the electronics industry. They are also suitable as carriers for crosslinked silicone rubber particles. In these applications, they permit (i) simplicity of incorporating particles in silicone or organic phases such as sealants, paints, coatings, greases, adhesives, antifoaming agents, and resin casting compounds, and (ii) they provide modified rheological, physical, or energy-absorbing properties of said phases, either in their pure state or in their final state.

In addition, the organopolysiloxane gels can serve as carriers for pharmaceuticals, biocides, herbicides, pesticides, and other biological active substances.

Furthermore, the compositions find application as additives for cellulose-based nonwoven carrier substrates or nonwoven synthetic carrier substrates, which are used in moist cleaning cloths such as moist cloths, moist tissues, and moist towels, which are generally marketed for body hygiene and household cleaning purposes.

Gel Preparation, General Specification (A and B)

According to method A, first a "basis gel" is prepared, which after gelation is diluted by adding a further amount of diluent. Method B differs from method A basically in that the full amount of diluent is added right from the start. No subsequent dilution of the gel obtained takes place.

Specification A:

A 2000-ml glass reactor is equipped with a condenser with attached nitrogen feed pipe, heating jacket, anchor stirrer, and a temperature control system. The reactor is flushed with nitrogen for 5 min before the start of the reaction. A corresponding amount of diluent, the Si—H-containing crosslinking agent or agents and the unsaturated organopolysiloxane resin are added and stirred until the resin has dissolved completely. The hydrosilylation catalyst is added and the reaction mixture is heated to 95° C. at a stirring speed of about 200 rev/min. It is stirred at this temperature for 2.5 hours. Then the heating jacket is removed, the mixture is cooled to room temperature at a reduced stirring speed (approx. 50 rev/min), and the catalyst poison is added. The gel obtained is homogenized with oscillation for one minute with an ULTRA-TURRAX® T 50 at 6000 rev/min. A "basis gel" is obtained, which can have a creamy to solid or crumbly consistency and is suitable for use in cosmetic products.

For dilution, the desired amount of diluent is added and it is stirred at 50 rev/min with the anchor stirrer, until the diluent has been taken up by the gel completely (approx. 10 minutes). Then it is homogenized again with oscillation for one minute with an ULTRA-TURRAX® T 50 at 6000 rev/min. In this way we obtain a creamy, transparent, or translucent gel that has a very smooth consistency, is stable in storage, and is suitable for use in cosmetic products.

Specification B:

A 2000-ml glass reactor is equipped with a condenser with attached nitrogen feed pipe, heating jacket, anchor stirrer, and temperature control system. The reactor is flushed with nitrogen for 5 min before the start of the reaction. The diluent, the Si—H-functional crosslinking agent, and the unsaturated organopolysiloxane resin are added, and it is stirred until the resin has dissolved completely. The hydrosilylation catalyst is added, and the reaction mixture is heated to 95° C. at a stirring speed of about 200 rev/min. It is stirred at this temperature for 2.5 hours. Then the heating jacket is removed, the mixture is cooled to room temperature at reduced stirring speed (approx. 50 rev/min), and the catalyst poison is added. The gel obtained is homogenized with oscillation for two minutes with an ULTRA-TURRAX® T 50 at 6000 rev/min. In this way we obtain a creamy, transparent, or translucent gel that has a very smooth consistency, is stable in storage, and is suitable for use in cosmetic products.

EXAMPLES 1-11 AND COMPARATIVE EXAMPLES V1-V5

A number of gels were produced according to specifications A and B. The substances used, their amounts, and the properties of the gels produced are shown below in Tables 1 to 3. The properties of the Si—H-functional crosslinking agents used in the examples and comparative examples are shown in Table 4.

Examples 1-5 are examples of gels for which a crosslinking agent with a very low content of Si—H groups is used, as single crosslinking agent, or in combination with another crosslinking agent. Nonvolatile polydimethylsiloxane (5 $mm^2$/s at 25° C.) was selected as diluent. Creamy gels that are stable in storage and suitable for use in cosmetic formulations are obtained. Example 3 shows a high-viscosity "basis gel." The gels in examples 4 and 5 have a comparable composition, but were produced by the different methods A or B. The gels display very similar properties, appearance, and viscosity. Example 4 was prepared according to specification A from the "basis gel" of example 3 by subsequent dilution. In contrast, example 5 was prepared according to specification B without a dilution step. Comparative examples V1 and V2 show gels in the same diluent as used in examples 1-5. However, comparative example V1 contains a crosslinking agent with a very high content of Si—H groups, as disclosed in U.S. Pat. No. 6,423,322 B1. Gel V1 has an oily, runny consistency that is undesirable for cosmetic applications. Comparative example V2 contains exclusively a crosslinking agent with medium content of Si—H groups. The gel separates into 2 phases during storage. It is not stable in storage and is therefore unsuitable for cosmetic applications. Example 6 shows an organopolysiloxane gel that was produced using volatile, linear polydimethylsiloxane (2.3 $mm^2$/s at 25° C.) as diluent. The gel is creamy, stable in storage, and transparent, and is very suitable for use in cosmetic applications.

Examples 7 to 9 show gels for which a crosslinking agent with a very low content of Si—H groups is used, as a single crosslinking agent or in combination with another crosslinking agent. Isopropyl myristate (=myristic acid propyl ester) was selected as diluent. Gels are obtained that are creamy, transparent, and stable in storage, which are suitable for use in cosmetic formulations. Comparative examples V3 and V4 show gels in the same diluent, which comprise exclusively crosslinking agent with a comparatively high content of Si—H groups. The gels are liquid and are not suitable for cosmetic applications. Furthermore, V3 separates into two phases.

Examples 10 and 11 show gels for which a crosslinking agent with a very low content of Si—H groups is used, as single crosslinking agent or in a combination with another crosslinking agent. Isododecane is used as diluent in these examples. Creamy gels that are stable in storage are obtained, which are suitable for use in cosmetic formulations. Comparative example V5 shows a gel in the same diluent, for which a crosslinking agent with a very high content of Si—H groups is used, as disclosed in U.S. Pat. No. 6,423,322 B1. A runny, oily gel, undesirable for cosmetic applications, is obtained, which separates into two phases during storage.

The viscosities of the organopolysiloxane gels were determined according to DIN EN ISO 3219 at a shear rate of 1/s and at 25° C.

TABLE 1

| ELASTOMER GEL FORMULATIONS: | | | | | | | | |
|---|---|---|---|---|---|---|---|---|
| Example:[1] | | 1 | 2 | 3 | 4 | 5 | V1 | V2 |
| Diluent | Polydimethyl-siloxane (5 mm$^2$/s)[2] | 75.67 | 79.76 | 75.65 | 82.75 | 82.65 | 79.73 | 79.47 |
| | Isopropyl myristate[3] | — | — | — | — | — | — | — |
| | Isododecane[4] | — | — | — | — | — | — | — |
| | Polydimethyl-siloxane (2.3 mm$^2$/s) | — | — | — | — | — | — | — |
| unsaturated silicone resin[5] | | 16.15 | 10.90 | 8.33 | 5.90 | 5.90 | 18.00 | 14.62 |
| Si—H-containing crosslinking agent | No. 1 (0.46% H) | — | — | — | — | — | 1.91 | — |
| | No. 2 (0.14% H) | 5.17 | 2.63 | — | — | — | — | 5.21 |
| | No. 3 (0.12% H) | — | — | — | — | — | — | — |
| | No. 4 (0.026% H) | 2.59 | 6.37 | 15.59 | 11.04 | 11.03 | — | — |
| Platinum poison | Mercapto oil[6] | 0.41 | 0.35 | 0.43 | 0.30 | 0.42 | 0.35 | 0.70 |
| Catalyst (ppm) | Platinum complex[7] | 5 | 5 | 5 | 5 | 5 | 5 | 10 |
| Batch size (g) | | 559 | 1239 | 1501 | 2119 | 943 | 1003 | 1235 |
| Mol resin-vinyl/mol Si—H | | 1.47 | 1.46 | 1.46 | 1.46 | 1.46 | 1.45 | 1.44 |
| Viscosity (mPa * s at 25° C.) | | 117000 | 127000 | 602000 | 160000 | 164000 | 84000 | 21000 |
| Properties | | creamy, stable | creamy, stable | lumpy, stable | creamy, stable | creamy, stable | oily to pasty, easily flowing | oily, runny, two-phase |
| Appearance | | transparent | transparent | translucent | transparent | transparent | translucent | translucent |
| Stable in storage | | yes | yes | yes | yes | yes | yes | no |
| Wt. % elastomer in the "basis gel" (in method A) | | — | 24 | — | 24 | — | — | 24 |
| Wt. % elastomer in the finished gel | | 24 | 20 | 24 | 17 | 17 | 20 | 20 |
| Specification used | | B | A | B | A | B | B | A |

[1]The amounts for diluent, unsaturated silicone resin, Si—H functional crosslinking agent, and platinum poison are to be understood as percentage by weight in the finished gel;
[2]WACKER-BELSIL ® DM 5 obtainable from Wacker Chemie AG; viscosity at 25° C.;
[3]Isopropyl myristate (CAS: 110-27-0) obtainable from Merck Schuchardt OHG;
[4]PUROLAN IDD (CAS: 93685-81-5) obtainable from LANXESS Distribution GmbH;
[5]Ratio M/M$^{Vi}$/Q = 7.6/1/11.4, $M_n$ = 2570, $M_w$ = 5440, iodine number = 18;
[6]Polysiloxane with 3-mercaptopropyl groups; viscosity 190 mm$^2$/s at 25° C., mercaptan content 0.29 wt. %;
[7]WACKER ® CATALYST OL obtainable from Wacker Chemie AG;

TABLE 2

ELASTOMER GEL FORMULATIONS:

| Example:[1] | | 6 | 7 | 8 | 9 | V3 | V4 |
|---|---|---|---|---|---|---|---|
| Diluent | Polydimethyl-siloxane, (5 mm²/s)[2] | — | — | — | — | — | — |
| | Isopropyl myristate[3] | — | 75.37 | 75.68 | 75.65 | 75.16 | 75.36 |
| | Isododecane[4] | — | — | — | — | — | — |
| | Polydimethyl-siloxane, (2.3 mm²/s) | 82.75 | — | — | — | — | — |
| unsaturated silicone resin[5] | | 5.90 | 13.48 | 12.73 | 8.33 | 16.97 | 17.54 |
| Si—H-containing crosslinking agent | No. 1 (0.46% H) | — | — | — | — | — | — |
| | No. 2 (0.14% H) | — | 3.44 | — | — | — | 6.26 |
| | No. 3 (0.12% H) | — | — | 3.72 | — | 7.22 | — |
| | No. 4 (0.026% H) | 11.04 | 6.88 | 7.44 | 15.59 | — | — |
| Platinum poison | Mercapto oil[6] | 0.30 | 0.83 | 0.43 | 0.43 | 0.65 | 0.84 |
| Catalyst (ppm) | Platinum complex[7] | 5 | 10 | 5 | 5 | 10 | 10 |
| Batch size (g) | | 706 | 520 | 1002 | 1001 | 532 | 515 |
| Mol resin-vinyl/mol Si—H | | 1.46 | 1.46 | 1.44 | 1.46 | 1.44 | 1.44 |
| Viscosity (mPa * s at 25° C.) | | 129000 | 60000 | 56000 | 132000 | — | — |
| Properties | | creamy, stable | creamy, stable | creamy, stable | creamy, stable | runny, two-phase | runny |
| Appearance | | transparent | transparent | transparent | transparent | transparent | transparent |
| Stable in storage | | yes | yes | yes | yes | — | — |
| Wt. % elastomer in the "basis gel" (in method A) | | 24 | — | — | — | — | — |
| Wt. % elastomer in the finished gel | | 17 | 24 | 24 | 24 | 24 | 24 |
| Specification used | | A | B | B | B | B | B |

[1]The amounts for diluent, unsaturated silicone resin, Si—H functional crosslinking agent, and platinum poison are to be understood as percentage by weight in the finished gel;
[2]WACKER-BELSIL ® DM 5 obtainable from Wacker Chemie AG; viscosity at 25° C.;
[3]Isopropyl myristate (CAS: 110-27-0) obtainable from Merck Schuchardt OHG;
[4]PUROLAN IDD (CAS: 93685-81-5) obtainable from LANXESS Distribution GmbH;
[5]Ratio M/M$^{Vi}$/Q = 7.6/1/11.4, $M_n$ = 2570, $M_w$ = 5440, iodine number = 18;
[6]Polysiloxane with 3-mercaptopropyl groups; viscosity 190 mm²/s at 25° C., mercaptan content 0.29 wt. %;
[7]WACKER ® CATALYST OL obtainable from Wacker Chemie AG;

TABLE 3

ELASTOMER GEL FORMULATIONS:

| Example:[1] | | 10 | 11 | V5 |
|---|---|---|---|---|
| Diluent | Polydimethyl-siloxane, (5 mm²/s)[2] | — | — | — |
| | Isopropyl myristate[3] | — | — | — |
| | Isododecane[4] | 75.36 | 82.57 | 79.73 |
| | Polydimethyl-siloxane, (2.3 mm²/s) | — | — | — |
| unsaturated silicone resin[5] | | 16.09 | 5.86 | 18.08 |
| Si—H-containing crosslinking agent | No. 1 (0.46% H) | — | — | 1.92 |
| | No. 2 (0.14% H) | 5.15 | — | — |
| | No. 3 (0.12% H) | — | — | — |
| | No. 4 (0.026% H) | 2.58 | 10.96 | — |
| Platinum poison | Mercapto oil[6] | 0.82 | 0.61 | 0.27 |
| Catalyst (ppm) | Platinum complex[7] | 10 | 10 | 5 |
| Batch size (g) | | 561 | 711 | 416 |
| Mol resin-vinyl/mol Si—H | | 1.47 | 1.46 | 1.45 |
| Viscosity (mPa * s at 25° C.) | | 125000 | 117000 | 15000 |

TABLE 3-continued

ELASTOMER GEL FORMULATIONS:

| Example:[1] | 10 | 11 | V5 |
|---|---|---|---|
| Properties | creamy, stable | creamy, stable | oily, runny |
| Appearance | transparent | transparent | transparent |
| Stable in storage | yes | yes | no |
| Wt. % elastomer in the "basis gel" (in method A) | — | 24 | 24 |
| Wt. % elastomer in the finished gel | 24 | 17 | 20 |
| Specification used | B | A | A |

[1]The amounts for diluent, unsaturated silicone resin, Si—H functional crosslinking agent, and platinum poison are to be understood as percentage by weight in the finished gel;
[2]WACKER-BELSIL ® DM 5 obtainable from Wacker Chemie AG; viscosity at 25° C.;
[3]Isopropyl myristate (CAS: 110-27-0) obtainable from Merck Schuchardt OHG;
[4]PUROLAN IDD (CAS: 93685-81-5) obtainable from LANXESS Distribution GmbH;
[5]Ratio M/M$^{Vi}$/Q = 7.6/1/11.4, $M_n$ = 2570, $M_w$ = 5440, iodine number = 18;
[6]Polysiloxane with 3-mercaptopropyl groups; viscosity 190 mm$^2$/s at 25° C., mercaptan content 0.29 wt. %;
[7]WACKER ® CATALYST OL obtainable from Wacker Chemie AG;

TABLE 4

PROPERTIES OF THE SI-H-CONTAINING CROSSLINKING AGENTS USED IN EXAMPLES 1-11 AND COMPARATIVE EXAMPLES V1-V5:

| No. | Distribution a: (b + c) | Sum a + b | Viscosity[1] (mm$^2$/s at 25° C.) | % H |
|---|---|---|---|---|
| 1 | 2: 1 | 138 | 331 | 0.47 |
| 2 | 9: 1 | 60 | 58 | 0.14 |
| 3 | 11: 1 | 130 | 328 | 0.12 |
| 4 | 55: 1 | 134 | 321 | 0.026 |

[1]Measured at 25° C.

EXAMPLE 12

The sensory properties of the organopolysiloxane gels from example 1, example 2, example 4, and comparative example V1 were assessed by a trained panel of testers. For this, the organopolysiloxane gels were diluted, if necessary, to comparable viscosity (90,000 mPa*s (+/−10%)) by adding polydimethylsiloxane (5 mm$^2$/s). This ensures that the sensory impression of the organopolysiloxane gels is not altered by different gel viscosities. After application on the skin, the sensory properties of the residues were assessed relative to one another. Table 5 shows the testers' average assessment, where a score of 5 corresponds to a preferred velvety-silky feel on the skin and a score of 0 corresponds to an undesirable greasy-oily feel on the skin.

TABLE 5

ASSESSMENT OF SENSORY PROPERTIES:

| Organopolysiloxane gel | Score (scale 0 to 5; 5 = best possible assessment) |
|---|---|
| Example 1 | 5 |
| Example 2 | 5 |

TABLE 5-continued

ASSESSMENT OF SENSORY PROPERTIES:

| Organopolysiloxane gel | Score (scale 0 to 5; 5 = best possible assessment) |
|---|---|
| Example 4 | 4 |
| Comparative example V1 | 1 |

EXAMPLES 13-14, COMPARATIVE EXAMPLE 6

A transparent Fluid Foundation was formulated with the organopolysiloxane gels produced in example 2, example 4, and comparative example V1, and the other ingredients shown in Table 6. For this, the organopolysiloxane gels from examples 2 and 4 were diluted to the same viscosity (90,000 mPa*s (+/−10%)) by adding diluent, to ensure better comparability, as described in example 12. The sensory properties were evaluated by a trained panel of testers. The testers assessed the ease of spreading on the skin, and the slipperiness and stickiness of the residue after spreading. Table 7 shows the testers' average assessment.

For production of the Fluid Foundation, first the oils of phase A are mixed in a paddle mixer. Then the resin of phase A is added with stirring and gentle heating, until a uniform mixture is formed. The organopolysiloxane gels are added to phase A and stirred in until homogeneous, the gels from example 2 or example 4 being diluted beforehand with the stated amount of WACKER-BELSIL® DM 5. The ingredients of phase B are combined together and mixed until they are uniform. Phase B is added to phase A and heated to 75° C. The ingredients of phase D are mixed by stirring until homogeneous and are heated to 75° C. The ingredients of phase C are combined and added to phase D. Then mixture CD is homogenized. Mixture AB is added to mixture CD. The mixture is homogenized and cooled slowly to room temperature, and the homogeneously stirred mixture of the ingredients of phase E is added at a temperature of 40° C.

It is found, extremely surprisingly, that the organopolysiloxane gels according to the invention from example 2 and example 4, which had been diluted beforehand with the stated amount of diluent to viscosity comparable to comparative example V1, as constituent of a Fluid Foundation, not only bring about a substantial improvement of the sensory properties, but that furthermore a smaller amount of silicone elastomer is sufficient. This follows from the proportion in the foundation (Table 6) taking into account the percentage content by weight of elastomer (Table 1).

TABLE 6

TRANSPARENT FLUID FOUNDATION:

| Phase | Trade name | INCI name | Comparative example V6 | Example 13 | Example 14 |
|---|---|---|---|---|---|
| A | Wacker-Belsil ® TMS 803 | Trimethylsiloxy-silicate | 1.9 | 1.9 | 1.9 |
| A | Crodamol PMP | PPG-2 Myristyl Ether Propionate | 0.8 | 0.8 | 0.8 |
| A | Eusolex ® OS | Ethylhexyl Salicylate | 4.8 | 4.8 | 4.8 |

TABLE 6-continued

TRANSPARENT FLUID FOUNDATION:

| Phase | Trade name | INCI name | Comparative example V6 | Example 13 | Example 14 |
|---|---|---|---|---|---|
| A | Miglyol® 812 N | Caprylic/Capric Triglyceride | 1.9 | 1.9 | 1.9 |
| A | Octyldodecyl neopentanoate | Octyldodecyl Neopentanoate | 1 | 1 | 1 |
|  | Comparative example V1 | Dimethicone, Dimethicone/Vinyltrimethyl Siloxysilicate Crosspolymer | 7.7 |  |  |
|  | Example 2 | Dimethicone, Dimethicone/Vinyltrimethyl Siloxysilicate Crosspolymer |  | 7.15 |  |
|  | Example 4 | Dimethicone, Dimethicone/Vinyltrimethyl Siloxysilicate Crosspolymer |  |  | 6.96 |
|  | Wacker-Belsil® DM 5 | Dimethicone |  | 0.55 | 0.74 |
| B | Wacker-Belsil® CDM 3526 VP | C26-28 Alkyl Dimethicone | 1.9 | 1.9 | 1.9 |
| B | Eusolex® 9020 | Butyl Methoxydibenzoyl methane | 1.9 | 1.9 | 1.9 |
| B | Span 85 | Sorbitan Trioleate | 1.9 | 1.9 | 1.9 |
| B | Tegin® | Glyceryl Stearate SE | 1.9 | 1.9 | 1.9 |
| C | AEC Magnesium Aluminum Silicate G2 | Magnesium Aluminum Silicate | 0.46 | 0.46 | 0.46 |
| C | Covafluid AMD | Aluminum Starch Octenylsuccinate | 0.9 | 0.9 | 0.9 |
| C | Eusolex® T 2000 | Titanium Dioxide, Alumina, Simethicone | 2.9 | 2.9 | 2.9 |
| C | Luzenac Pharma UM | Talc | 1.9 | 1.9 | 1.9 |
| C | Très BN® PUHP1109 | Boron Nitride | 0.1 | 0.1 | 0.1 |
| C | Pigment Pre Mix[1] |  | 4.74 | 4.74 | 4.74 |
| D | Butylene Glycol | Butylene Glycol | 2.9 | 2.9 | 2.9 |
| D | EDETA B Powder | Tetrasodium EDTA | 0.3 | 0.3 | 0.3 |
| D | Glycerin 100% waterless | Glycerin | 2.9 | 2.9 | 2.9 |
| D | Keltrol SF | Xanthan Gum | 0.5 | 0.5 | 0.5 |
| D | Tween 60 | Polysorbate 60 | 1.9 | 1.9 | 1.9 |
| D | Water | Aqua (DI Water) | 53.75 | 53.75 | 53.75 |
| E | Copherol 1250 | Tocopheryl Acetate | 0.3 | 0.3 | 0.3 |
| E | Perfume SCE 243993 Pitanga | Perfume | 0.25 | 0.25 | 0.25 |
| E | Phenonip | Phenoxyethanol and Methylparaben and Ethylparaben and Butylparaben and Propylparaben and Isobutylparaben | 0.5 | 0.5 | 0.5 |

[1]3.95 parts CI 77891 Unipure White LC 981 (LCW), 2.90 parts titanium dioxide, alumina, simethicone Eusolex T 2000 (Merck KGaA), 0.15 parts CI 77491 Unipure Red LC 383 (LCW), 0.10 parts Boron Nitride Très BN PUHP1109 (Saint-Gobain Advanced Ceramics Bor), 0.04 parts CI 77499 Unipure Black LC 989 (LCW), 0.50 parts CI 77492 Unipure Yellow LC 181 (LCW), 0.10 parts CI 77491 + CI 77492 + CI 77499 Unipure Brown LC 887 (LCW).

TABLE 7

ASSESSMENT OF SENSORY PROPERTIES:

| Fluid Foundation | Spreading of foundation | Slipperiness of residue | Stickiness of residue |
|---|---|---|---|
| Comparative example V6 (comprising V1) | ○ | ○ | ○ |
| Example 13 (comprising example 2) | ++ | + | ○ |
| Example 14 (comprising example 4) | ○ | + | ++ |

The invention claimed is:

1. An organopolysiloxane gel produced by a process comprising reacting:
(1) at least one unsaturated MQ resin comprising units of the formulas $SiO_2$ (Q units) and $R_3SiO_{1/2}$ and $R_2R'SiO_{1/2}$ (M units), wherein
R is an identical or different monovalent, optionally substituted hydrocarbon group having 1 to 18 carbon atoms per group,
R' is a monovalent hydrocarbon group capable of hydrosilylation by Si—H groups, with the provisos that the at least one unsaturated MQ resin contains at least 2 R' groups that the molar ratio of M units to Q units is in a range from 0.5 to 4.0, and the at least one unsaturated MQ resin comprises $(CH_3)_3SiO_{1/2}$ groups,
with
(2) at least one Si—H functional organopolysioxane of the formula $$H_cR_{3-c}SiO(R_2SiO)_a(RHSiO)_bSiR_{3-c}H_c \quad (I),$$

wherein
c is 0 or 1,
R is an identical or different monovalent, optionally substituted hydrocarbon group having 1 to 18 carbon atoms per group,
a and b are integers,
with the proviso
that the sum a+b is 66 to 248,
that the at least one Si—H functional organopolysiloxane of the formula (I) contains Si-bonded hydrogen in an amount from 0.011 to 0.044 wt. %, and
that the number of Si—H groups per molecule on average is greater than 2,
or a mixture of (2) the at least one Si—H functional organopolysiloxane of the formula (I) with
(2') Si—H functional organopolysiloxanes of the formula $$H_cR_{3-c}SiO(R_2SiO)_a(RHSiO)_bSiR_{3-c}H_c \quad (I'),$$

wherein
c is 0 or 1,
R is an identical or different monovalent, optionally substituted hydrocarbon group having 1 to 18 carbon atoms per group,
a and b are integers,
with the proviso that the sum a+b is 38 to 248, that the Si—H functional organopolysiloxanes of the formula (I') contain Si-bonded hydrogen in an amount from 0.045 to 0.35 wt. %, and that if a mixture of (2) and (2') is used, the weight ratio of (2) to (2') is greater than 0.2, in the presence of (3) a catalyst which promotes addition at Si-bonded hydrogen onto an aliphatic multiple bond, wherein a mixture of (1) and (2) or a mixture of (1), (2), and (2') is dispersed in (4) at least one diluent selected from organopolysiloxanes with 2 to 200 Si atoms and organic diluents.

2. The organopolysiloxane gel of claim 1, wherein the form of a creamy gel that is stable in storage.

3. The organopolysiloxane gel of claim 2, wherein the organopolysiloxane gel further comprises at least one selected from the group consisting of active subatances for body care and active substance for health care.

4. The organopolysiloxane gel of claim 1, wherein the at least one diluents is selected from the group consisting of polydimethylsiloxane having 2 to 50 Si atoms, aliphatic hydrocarbons having 4 to 30 carbon atoms, alicyclic hydrocarbons having 4 to 30 carbon atoms, and esters of carboxylic acids having 2 to 30 carbon atoms.

5. A method of producing the organopolysiloxane gel of claim 1 comprising reacting (1) the at least one unsaturated MQ resin with (2) the at least one Si-H functional organopolysiloxane of the formula (I) or with a mixture of (2) the at least one Si—H functional organopolysiloxane of the formula (I) and (2') the Si—H functional organopolysiloxane of the formula (I'), in the presence of (3) a catalyst which promotes addition at Si-bonded hydrogen onto an aliphatic multiple bond, and dispersing a mixture of (1) and (2) or a mixture of (1), (2), and (2') in (4) at least one diluent selected from organopolysiloxane having 2 to 200 Si atoms and organic diluents.

6. The method of claim 5 further comprising homogenizing the organopolysiloxane gel after the reaction, and obtaining a creamy organopolysiloxane gel that is stable in storage.

7. The method of claim 6 further comprising diluting the organopolysiloxane gel with active substances for body care, active substances for health care, and/or the at least one diluent selected from organopolysiloxane having 2 to 200 Si atoms and organic diluents to form a diluted organopolysiloxane gel, and optionally homogenizing the diluted organopolysiloxane gel.

8. The method of claim 7, wherein the at least one diluent is selected from the group consisting of polydimethylsiloxane having 2 to 50 Si atoms, aliphatic hydrocarbons having 4 to 30 carbon atoms, alicyclic hydrocarbons having 4 to 30 carbon atoms, and esters of carboxylic acids having 2 to 30 carbon atoms.

9. A cosmetic composition comprising one or more organopolysiloxane gels of claim 1.

10. A cosmetic composition comprising one or more organopolysiloxane gels as produced in claim 5.

11. The organopolysiloxane gel of claim 1, wherein R' is a terminal alkenyl group having 2 to 12 carbon atoms.

12. The organopolysiloxane gel of claim 1, wherein R' is a vinyl group.

13. The organopolysiloxane gel of claim 1, wherein the at least one unsaturated MQ resin contains at least 3 R' groups and the molar ratio of M units to Q units is in a range from 0.5 to 2.0.

14. The organopolysiloxane gel of claim 1, wherein the sum a+b is from 118 to 168.

15. The organopolysiloxane gel of claim 1, wherein the at least one Si—H functional organopolysiloxane of the formula (I) contains Si-bonded hydrogen in an amount from 0.022 to 0.032 wt. %.

16. The organopolysiloxane gel of claim 1, wherein the Si—H functional organopolysiloxanes of the formula (I') contain Si-bonded hydrogen in an amount from 0.045 to 0.156 wt. %.

17. The organopolysiloxane gel of claim 1, wherein the weight ratio of (2) to (2') is greater than 0.3.

18. The method of claim 5, wherein R' is a terminal alkenyl having 2 to 12 carbon atoms.

19. The method of claim 5, wherein R' is a vinyl group.

* * * * *